(12) United States Patent
Baïkoff

(10) Patent No.: US 6,673,111 B2
(45) Date of Patent: *Jan. 6, 2004

(54) SCLERAL EXPANSION SEGMENT

(75) Inventor: Georges Baïkoff, Marseilles (FR)

(73) Assignee: O.I.I. International, Inc., Ontario, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/833,903

(22) Filed: Apr. 12, 2001

(65) Prior Publication Data

US 2002/0035397 A1 Mar. 21, 2002

Related U.S. Application Data

(63) Continuation of application No. PCT/FR99/02486, filed on Oct. 13, 1999.

(30) Foreign Application Priority Data

Oct. 13, 1998 (FR) .............................................. 98 12834

(51) Int. Cl.$^7$ ................................................. A61F 2/14
(52) U.S. Cl. ......................................... 623/4.1; 600/37
(58) Field of Search ................................. 623/4.1, 6.64, 623/FOR 103; 600/37; 606/204.25; 601/37

(56) References Cited

U.S. PATENT DOCUMENTS

| | | | | |
|---|---|---|---|---|
| 5,370,607 A | * | 12/1994 | Memmen | ........................ 604/8 |
| 6,007,578 A | | 12/1999 | Schachar | |
| 2002/0002403 A1 | * | 1/2002 | Zdenek et al. | ................ 623/4.1 |

FOREIGN PATENT DOCUMENTS

| | | | | |
|---|---|---|---|---|
| CH | 43543 | * | 3/1908 | ............. 606/204.25 |
| FR | 644591 | * | 10/1928 | ............. 606/204.25 |
| WO | WO 9503755 | | 2/1995 | |
| WO | WO 9515719 | | 6/1995 | |

* cited by examiner

Primary Examiner—David H. Willse
(74) Attorney, Agent, or Firm—Denton L. Anderson; Sheldon & Mak

(57) ABSTRACT

A scleral expansion segment consists of an arched rod designed to be placed on the sclera perpendicular to the ciliary body. The arched rod has a pair of free ends connected by a bridge. The free ends have a spatula shape wider than the diameter of the bridge, so as to constitute wide support bases.

10 Claims, 3 Drawing Sheets

SCLERAL EXPANSION SEGMENT

CROSS REFERENCE TO RELATED APPLICATIONS

This application is a continuation of International Application Serial No. PCT/FR99/02486, filed Oct. 13, 1999 and never published, which claims priority as a continuation of French patent application Serial No. 98/12834, filed Oct. 13, 1998, which issued as French Patent No. 2784287 on Dec. 8, 2000.

BACKGROUND OF THE INVENTION

The present invention concerns, in general, the correction of vision by insertion of a corrective element in the eye and, more specifically, the correction of presbyopia.

According to new theories, presbyopia is not linked solely to the loss of flexibility of the crystalline lens on aging, but is mainly due to increase of the diameter of said crystalline lens with age.

As schematically represented in FIG. 8, the crystalline lens Cr contained in the crystalline lens sac S is suspended from the sclera Sc along a ring of the latter located behind the limbus L separating the vitreous body V from the opaque body O. Said suspension of the crystalline lens is secured by a ligament Z called zonule attached to the ciliary body Cc. As the size of the scleral ring and ciliary body Cc do not vary in time, the zonule Z is gradually expanded in the course of enlargement of the crystalline lens Cr and partially loses its traction power on the equator of the crystalline lens sac S.

A new surgical method has therefore been proposed to correct presbyopia, consisting of increasing the diameter of the scleral ring in the ciliary body, so as to stretch the zonule, which will again be able to perform its function of deformation of the crystalline lens under the effect of contraction of the ciliary muscle and return the power of accommodation to the eye.

For the use of this method of treatment, Schachar proposed a truncated cone-shaped ring set in place by suture around the scleral ring (U.S. Pat. No. 5,465,737).

However, this ring requires a very long and difficult surgical intervention and entails unpleasant sequelae for the patients.

Arched segments have therefore been recently proposed, which are set in place in loops incised in the thickness of the sclera concentric to the limbus, perpendicular to the ciliary body, and which constitute stiffeners exerting an outward traction stretching the zonule. In practice, four scleral segments are placed at 90°.

This intervention is much more effective than placement of the complete ring initially proposed by Schachar, for the surgical procedure is simple and rapid (incision of four tunnels constituting the loops and insertion of the segments) and eliminates any suture, therefore considerably diminishing the patient's discomfort and operating sequelae. This technique is schematically illustrated in FIG. 9.

This figure shows a sclera fragment Sc, in which a tunnel T has been formed, like a belt loop.

The segment Sg has been inserted in this loop and rests at its bases A and B on the sclera, on which it bears, while its bridge C exerts an outward traction force. It can be seen that the zonule is expanded $Z_1$ perpendicular to force C and relaxed $Z_2$ perpendicular to forces A and B.

However, the present segments, which are simple cylindrical rods, present a sizable risk of perforation of the sclera by reason of the fact that they punctually bear on the latter.

The purpose of this invention is to eliminate this disadvantage and to propose scleral expansion segments which present no risk of perforation of the sclera.

SUMMARY OF THE INVENTION

According to the invention, the scleral expansion segment which, in a manner known per se, consists of an arched rod designed to be placed on the sclera perpendicular to the ciliary body, is characterized in that its free ends have a spatula shape wider than the diameter of said rod, so as to constitute wide support bases.

The segment according to the invention is further remarkable in that:
- the bases have a radius of curvature R1 corresponding to that of the sclera perpendicular to the ciliary body, while the bridge has radius of curvature R2 less than R1;
- it presents a multitude of perforations;
- it is coated with a biocompatible synthetic material with porous surface;
- it consists of a core of deformable material with shape memory, sunk in a layer of soft material;
- it has an internal canal designed for placement of a core, the nature and strength of which can be chosen in order to adjust the effect of the scleral expansion segment;
- the core consists of an injectable product;
- it is made in two parts interlocking with each other;
- the first part consists of a base equipped with a female attachment means, while the second part consists of the other base combined with the bridge, the free end of which contains a male attachment means; and
- the two parts contain means for preventing any rotation in relation to each other.

BRIEF DESCRIPTION OF THE DRAWINGS

The invention will be better understood thanks to the specification which follows, given by way of nonlimitative example with reference to the attached drawings in which.

DETAILED DESCRIPTION OF THE INVENTION

Figure 1:
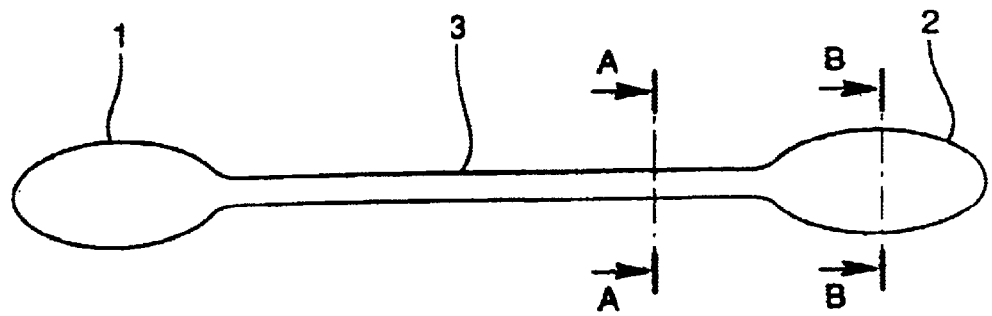
FIG. 1 is a top view of a scleral expansion segment according to a first embodiment of the invention.

As represented in FIG. 1, the scleral expansion segment according to the invention consists of an arched rod having two ends forming two bases 1 and 2 connected by a cylindrical bridge 3. The bases 1 and 2 consist of parts wider than the diameter of the bridge 3, spatula-shaped, and their inner face is flattened. This arrangement makes possible the bearing of the scleral expansion segment on the sclera to be made on a relatively extended surface, which enables the pressure directed toward the inside of the eye, exerted on the surface of said sclera, to be reduced considerably.

Figure 2:
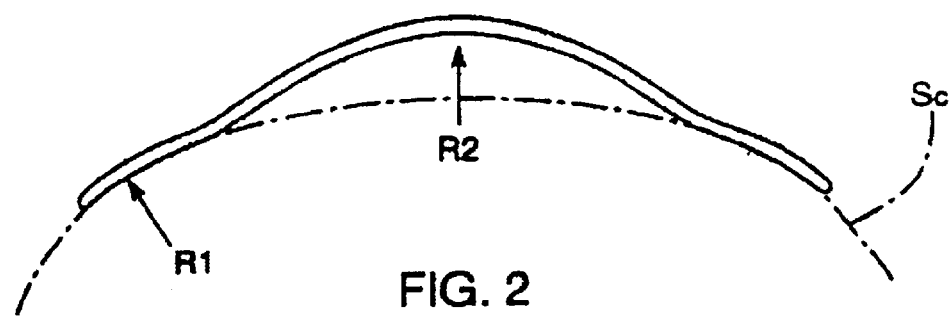
FIG. 2 is a side view of the scleral expansion segment of FIG. 1.

As is evident in FIG. 2, the scleral expansion segment is an arched piece having two radii of curvature. The bases 1 and 2 have a radius of curvature R1 corresponding to that of the sclera Sc perpendicular to the ciliary body, while the bridge 3 has a radius of curvature R2 less than R1, so as to stretch over the scleral loop.

In the embodiments represented in the drawings, said bases, seen from the top, have an overall ellipsoidal shape. Their ends are rounded in order to avoid damaging the sclera.

The material used for manufacture of the scleral expansion segment is a biocompatible synthetic material, such as PMMA, polyHEMA or ceramic.

Figure 3:
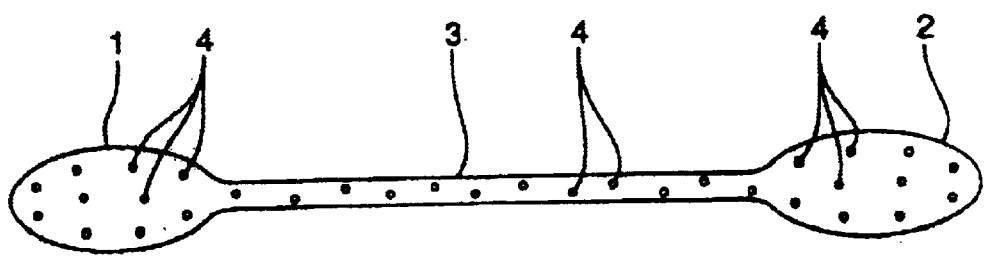
FIG. 3 is a top view of a scleral expansion segment according to a second embodiment of the invention.

In the working variant represented in FIG. 3, the scleral expansion segment has a multitude of perforations 4 through which the connective tissue can grow in order to improve attachment of the sclera to said correction segment and/or to serve as a point of passage for a possible suture, if necessary.

According to a variant not represented in the drawing, the creation of holes 4 can be replaced by providing a porous surface on the scleral expansion segment with openings wide enough to accept colonization by the connective tissue. Such a surface will, for example, be made by coating the segment with a bio-compatible synthetic material, a hydroxyapatite, a variable hydration component, etc.

The scleral expansion segment according to the invention can also be so conceived that its action is adjustable, that is, so that its shape can be modified to adjust its effect on the zonule upon placement or if it should diminish in time.

Figure 4A:
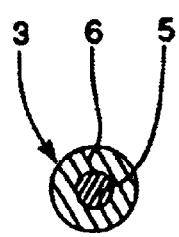
FIGS. 4a and 4b are sections respectively along lines I—I and II—II of FIG. 1.
Figure 4B:
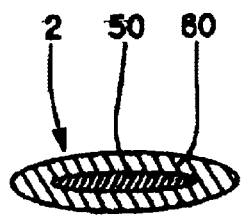

For that purpose, and as represented in FIGS. 4a and 4b, which respectively illustrate a section of the bridge 3 and a section of a base 1 or 2, the scleral expansion segment contains a core 5, 50 of rigid material capable of retaining the shape imparted to it, sunk in a soft material 6, 60.

The material constituting the core 5 is preferably chosen among deformable materials with shape memory.

According to an embodiment not represented in the drawing, the scleral expansion segment has an internal canal intended for placement of a core, the nature and strength of which can be chosen by the practitioner in order to adapt the effect of the scleral expansion segment to the state of the eye under care.

As the bridge 3 of the scleral expansion segment can have a diameter in the order of 0.6 millimeter, the internal canal intended to contain the core can have a diameter in the order of 0.2 millimeter.

Such a removable core can be made in the form of a solid body that is inserted in the scleral expansion segment.

It can also consist of an injectable product that is introduced in the canal formed in the scleral expansion segment, the effect of the scleral expansion segment then being adjusted by modulating the pressure of the product introduced in said segment.

The product injected in the canal of the scleral expansion segment can be a gas, or even a liquid or gel, polymerizable or not.

Owing to the fact that the scleral expansion segment according to the invention contains bases larger in size that the bridge cooperating with the loop incised in the sclera in which it is placed, it is to be understood that the surgeon will either have to make a wider incision or force a base of the segment into the loop. In the first case, he runs the risk of improper holding of the segment and insufficient traction of the segment on the zonule. In the second case, he risks damaging the sclera.

This is why, according to a particularly advantageous variant, the invention provides for making the scleral expansion segment in two parts interlocking with each other and arranged so that one end of the bridge is free for insertion of the segment in the loop.

Figure 5:
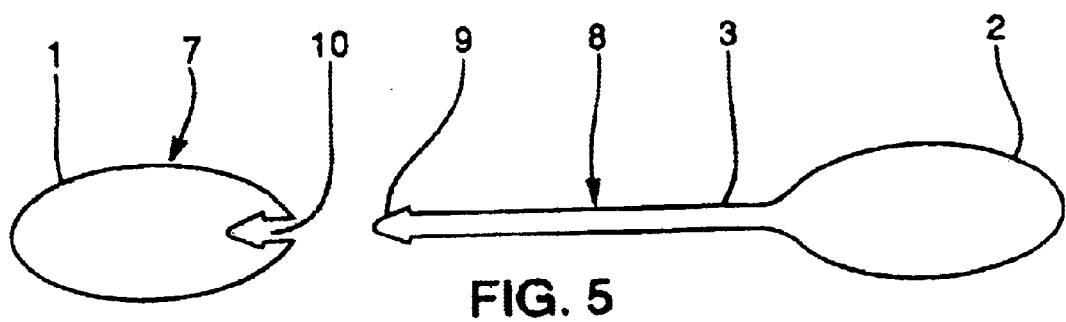
FIG. 5 is a top view of a scleral expansion segment according to a third embodiment of the invention.
Figure 6:
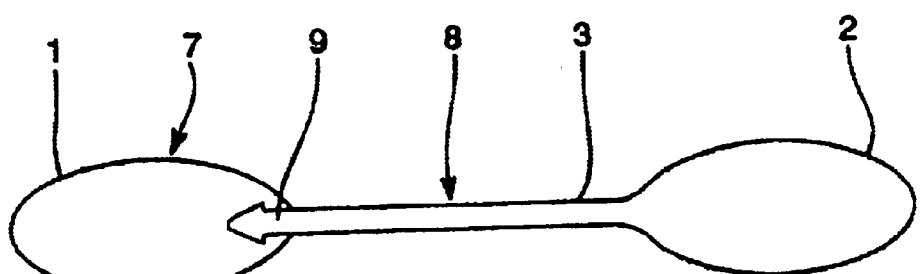
FIG. 6 shows the scleral expansion segment of FIG. 5 assembled.

Such a segment is represented in FIGS. 5 and 6.

It consists of two parts 7 and 8, which can be attached to each other by means of attachment 9 and 10.

As can be seen in FIG. 5, the first part 7 contains a base, base 1 in the working example represented in the drawing, while the second part 8 contains the second base 2 and the bridge 3.

The end of the bridge 3 is shaped to constitute a means of attachment 9 fitted to cooperate with a complementary means of attachment 10 carried by the first part 7.

In the working example represented in the drawing, the bridge 3 of part 8 carries a generally harpoon-shaped male attachment 9 and part 7 has a female attachment 10 consisting of a cavity complementing the shape of the harpoon 9.

Preferably, in order to avoid any risk of trauma, rounded end shapes will be used for attachment means 9 and 10.

Also preferably, in order to avoid any error in connection between the two pieces or untimely rotation of one piece in relation to the other after connection, grooves will be made on the periphery of the free end of the bridge (for example, 3 grooves over 120°), cooperating with corresponding grooves on the inner periphery of the cavity 10 engaging the base of the segment.

Figure 7A:
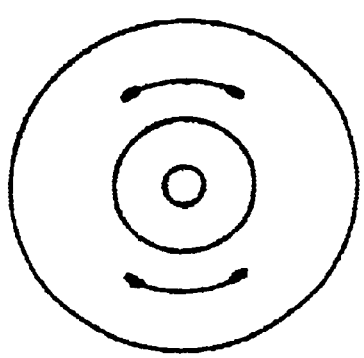
FIGS. 7a to 7c schematically represent examples of arrangements in the eye of the scleral expansion segments according to the invention.
Figure 7B:
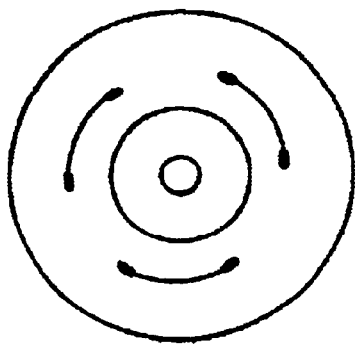
Figure 7C:
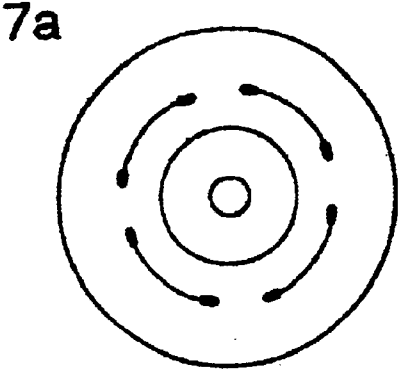
Figure 8:
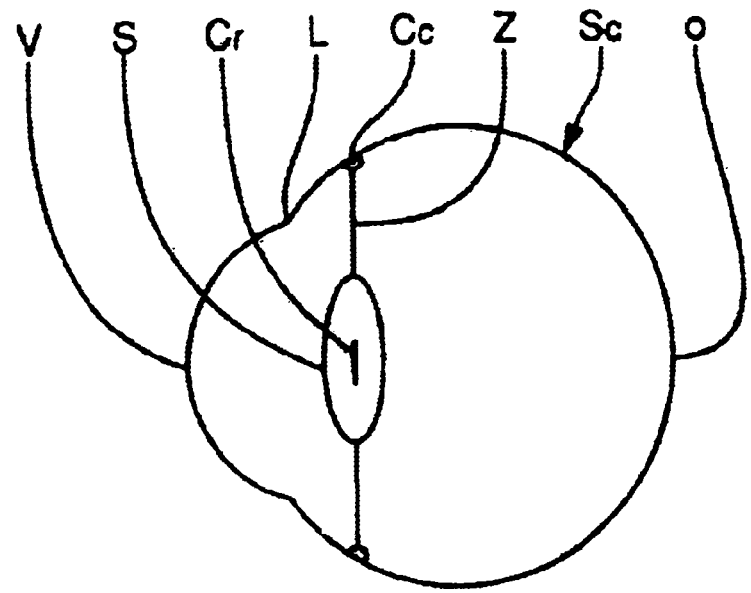
FIG. 8 is a schematic section of an eye.
Figure 9:
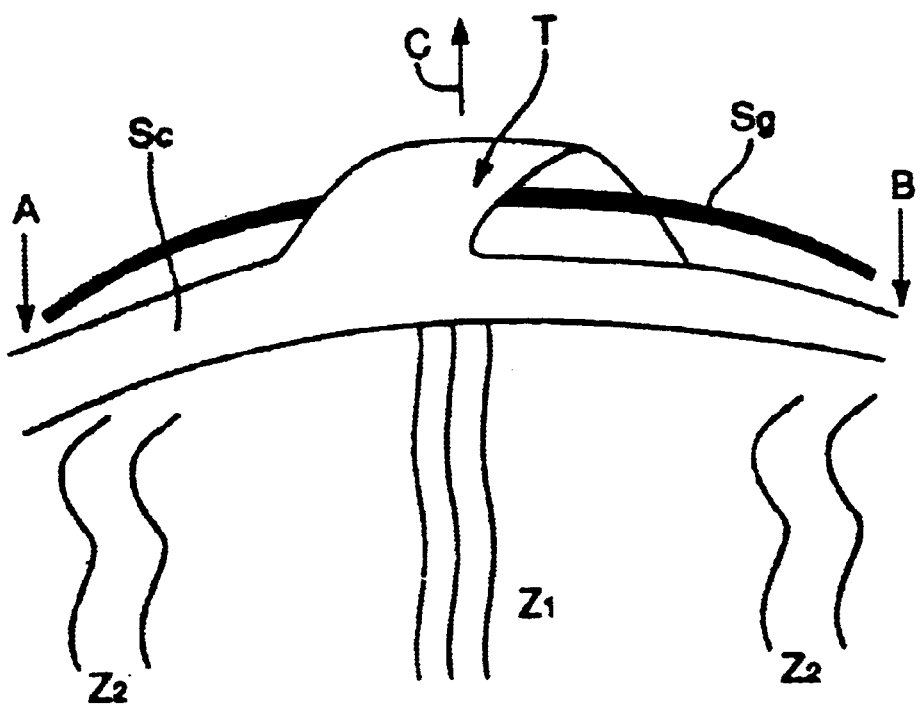
FIG. 9 is a partial schematic section of an eye equipped with a scleral expansion segment.

It was indicated at the beginning of this specification that the segments are generally arranged in 4's roughly at 90°, perpendicular to the ciliary body at approximately 3 mm behind the limbus (FIG. 7c), but other arrangements can be adopted, for example, two segments in polar positions (FIG. 7a) or three segments at 120° (FIG. 7b).

By way of indication, the scleral expansion segments have a length in the order of 3 to 5 millimeters, their base having, for example, a width ranging between 1 and 2 millimeters.

In addition to the safety and facility of placement they provide, the scleral expansion segments according to the invention have the advantage of being very easy to deposit and modify in the course of the operation in order to adapt the curvature of their bridge to the outward traction desired.

Working examples have been described above, in which the scleral expansion segment has a cylindrical rod-shaped bridge, but, without departing from the scope of the invention, the bridge could have any other shape (sheet, band, etc.), once that bridge is connected to extended bases.

Finally, if a surgical procedure should be necessary on the eye bearing segments according to the invention, said segment can easily be removed either by disengaging them or by sectioning them in proximity to one of the support bases.

I claim:

1. A scleral expansion segment comprising an arched rod having two free ends connected by a bridge, the arched rod being designed to be placed on the sclera perpendicular to the ciliary body and being characterized in that the free ends of said rod have a spatula shape wider than a diameter of said bridge, so as to constitute wide support bases.

2. The segment according to claim 1, characterized in that the bases have a radius of curvature R1 corresponding to that of the sclera perpendicular to the ciliary body, whereas the bridge has a radius of curvature R2 less than R1.

3. The segment according to claim 2, characterized in that it defines a multitude of perforations.

4. The segment according to claim 2, characterized in that it is coated with a biocompatible synthetic material with a porous surface.

5. The segment according to claim 4, characterized in that it consists of a core of formable material with shape memory, sunk in a layer of soft material.

6. The segment according to claim 4, characterized in that it has an internal canal intended for placement of a core, the nature and strength of which can be chosen in order to adjust the effect of the scleral expansion segment.

7. The segment according to claim 6, characterized in that the core consists of an injectable product.

8. The segment according to claim 7, characterized in that it is made in two parts, a first part and a second part, which interlock with each other.

9. The segment according to claim 8, characterized in that the first part includes a base equipped with a female attachment means, while the second part includes the other base combined with the bridge, the free end of which contains a male attachment means.

10. The segment according to claim 9, characterized in that the two parts contain means for preventing any rotation relative to each other.

\* \* \* \* \*

EX PARTE REEXAMINATION CERTIFICATE (6492nd)

United States Patent
Baïkoff

(10) Number: US 6,673,111 C1
(45) Certificate Issued: *Oct. 28, 2008

(54) SCLERAL EXPANSION SEGMENT

(75) Inventor: Georges Baïkoff, Marseilles (FR)

(73) Assignee: O.I.I. International, Inc., Ontario, CA (US)

Reexamination Request:
No. 90/008,420, Mar. 12, 2007

Reexamination Certificate for:
Patent No.: 6,673,111
Issued: Jan. 6, 2004
Appl. No.: 09/833,903
Filed: Apr. 12, 2001

( * ) Notice: This patent is subject to a terminal disclaimer.

Related U.S. Application Data

(63) Continuation of application No. PCT/FR99/02486, filed on Oct. 13, 1999.

(51) Int. Cl.
*A61F 9/00* (2006.01)
*A61F 2/14* (2006.01)

(52) U.S. Cl. .......................... 623/4.1; 600/37
(58) Field of Classification Search ....................... None
See application file for complete search history.

(56) References Cited

U.S. PATENT DOCUMENTS 6,197,056 B1    3/2001   Schachar .................... 623/4.1
6,280,468 B1    8/2001   Schachar .................... 623/4.1

OTHER PUBLICATIONS

"Spatula," http://en.wikipedia.org/wiki/Spatula, Oct. 25, 2006, 2 pages.
"Slimline Spatula," http://www.kutzindustries.com/html/sl%20spatula.htm, Oct. 25, 2006, 2 pages.

*Primary Examiner*—David O. Reip

(57) ABSTRACT

A scleral expansion segment consists of an arched rod designed to be placed on the sclera perpendicular to the ciliary body. The arched rod has a pair of free ends connected by a bridge. The free ends have a spatula shape wider than the diameter of the bridge, so as to constitute wide support bases.

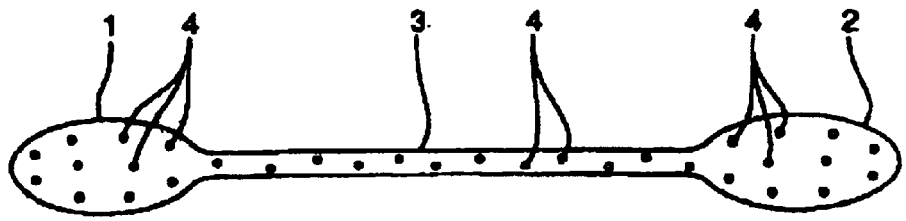

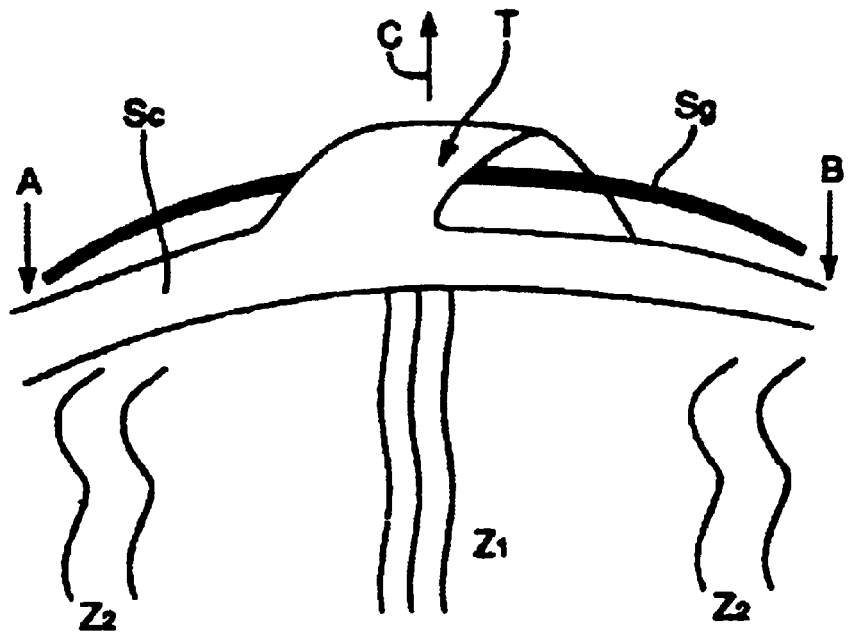

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–4 and 6–10 is confirmed.

Claim 5 was not reexamined.

* * * * *